(12) United States Patent
Singh et al.

(10) Patent No.: US 6,313,308 B1
(45) Date of Patent: Nov. 6, 2001

(54) METHODS FOR THE PREPARATION OF BIPHENYL ISOXAZOLE SULFONAMIDES

(75) Inventors: Ambarish Singh, Bordentown; Chien-Kuang Chen, Marlboro; John A. Grosso, Princeton Jct; Edward J. Delaney, Princeton; Xuebao Wang, East Brunswick; Richard P. Polniaszek, Dayton; John K. Thottathil, Princeton, all of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/528,819

(22) Filed: Mar. 20, 2000

Related U.S. Application Data

(60) Provisional application No. 60/125,148, filed on Mar. 19, 1999.

(51) Int. Cl.[7] ............ C07D 261/16; C07D 413/12
(52) U.S. Cl. ............ 548/235; 548/245; 548/246
(58) Field of Search ................. 548/235, 245, 548/246

(56) References Cited

U.S. PATENT DOCUMENTS

| | | | |
|---|---|---|---|
| 2,888,455 | 5/1959 | Kano, Hideo et al. | 548/246 |
| 4,415,496 | 11/1983 | Harris et al. | 540/521 |
| 4,661,479 | 4/1987 | Wyvratt, Jr., et al. | 514/214 |
| 5,236,928 | 8/1993 | Chakravarty et al. | 514/275 |
| 5,270,313 | 12/1993 | Burri et al. | 514/252 |
| 5,292,740 | 3/1994 | Burri et al. | 514/256 |
| 5,378,715 | 1/1995 | Stein et al. | 514/329 |
| 5,464,853 | 11/1995 | Chan et al. | 514/378 |
| 5,514,691 | 5/1996 | Chan et al. | 514/312 |
| 5,514,696 | 5/1996 | Murugesan et al. | 514/380 |
| 5,571,821 | 11/1996 | Chan et al. | 514/312 |
| 5,580,894 | 12/1996 | Scott, Kenneth et al. | 514/380 |
| 5,591,761 | 1/1997 | Chan, Ming F., et al. | 514/380 |
| 5,594,201 | 1/1997 | Chan, Ming F., et al. | 514/378 |
| 5,612,359 | * 3/1997 | Murugesan | 514/365 |
| 5,846,985 | 12/1998 | Murugesan | 514/364 |
| 5,846,990 | 12/1998 | Murugesan et al. | 514/374 |
| 5,856,507 | * 6/1999 | Polniasek et al. | 548/241 |
| 6,080,774 | * 6/2000 | Murugesan et al. | 514/380 |

FOREIGN PATENT DOCUMENTS

| | | |
|---|---|---|
| 34011/93 | 9/1993 | (AU) . |
| A-67357/94 | 1/1995 | (AU) . |
| A48039/96 | 9/1996 | (AU) . |
| 364506 | 11/1962 | (CH) . |
| 1059459 | 6/1959 | (DE) . |
| 0076072 B1 | 4/1983 | (EP) . |
| 0194548 A2 | 9/1986 | (EP) . |
| 0404525 B1 | 12/1990 | (EP) . |
| 0443983 B1 | 8/1991 | (EP) . |
| 0510526 B1 | 10/1992 | (EP) . |
| 0526708 A1 | 2/1993 | (EP) . |
| 0558258 B1 | 9/1993 | (EP) . |
| 0569193 B1 | 11/1993 | (EP) . |
| 0601386 A1 | 6/1994 | (EP) . |
| 0617001 B1 | 9/1994 | (EP) . |
| 0626174 A2 | 11/1994 | (EP) . |
| 0626174 A3 | 11/1994 | (EP) . |
| 06322259 B1 | 1/1995 | (EP) . |
| 0634175 A1 | 1/1995 | (EP) . |
| 0640596 A1 | 3/1995 | (EP) . |
| 0682016 A1 | 11/1995 | (EP) . |
| 0702012 A1 | 3/1996 | (EP) . |
| 0749964 A1 | 12/1996 | (EP) . |
| 804036 | 11/1958 | (GB) . |
| 897440 | 5/1962 | (GB) . |
| 1473433 | 5/1977 | (GB) . |
| 2228933 | 9/1990 | (GB) . |
| WO 91/15479 | 10/1991 | (WO) . |
| WO 93/08799 | 5/1993 | (WO) . |
| WO 93/10094 | 5/1993 | (WO) . |
| WO 93/23404 | 11/1993 | (WO) . |
| WO 94/27979 | 12/1994 | (WO) . |
| WO 95/26957 | 10/1995 | (WO) . |
| 0725067 A1 | 8/1996 | (WO) . |
| WO 96/40681 | 12/1996 | (WO) . |
| 0768305 A1 | 4/1997 | (WO) . |
| WO 97/29747 | 8/1997 | (WO) . |
| WO 99/36393 | 7/1999 | (WO) . |
| WO-00/56685-A1 | * 9/2000 | (WO) . |

OTHER PUBLICATIONS

Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
A.M., van Leusen et al., J. Org. Chem. vol. 41, No. 4 (1976), pp. 711–713.
Stein et al., CA 120:18233n, pp. 21–22 (1994).
Derwent Abstract No. 91–254550/35 Feb. 19, 1990.
Stein et al., J. Med. Chem., vol. 37, No. 3, Feb. 4, 1994, pp. 329–331.
Ferrini et al., vol. 2, No. 2, p. 99 (1963).
Chan et al., Biochemical and Biophysical Research Communications, vol. 201, No. 1, May 30, 1994, pp. 228–234.
Doherty, J. Med. Chem., 35(9), 1493–1508 (May, 1992).
Williams, Tetrahedron Letters, vol. 33, No. 8, pp. 1033–1036 (1992).
Cass, J. Am. Chem. Soc., vol. 64, pp. 785–787 (1942).
Murugesan et al., CA 120:270370c, p. 1067 (1994).
Allen et al., CA 116(11):1062847Z, p. 778, 1992.
Khanna, CA 115:35728, p. 415 (1991).

(List continued on next page.)

Primary Examiner—Fiona T. Powers
(74) Attorney, Agent, or Firm—Ronald S. Hermenau

(57) ABSTRACT

Methods for the preparation of biphenyl isoxazole sulfonamides and intermediates therof. The present invention also relates to the novel intermediates prepared by these methods. The biphenyl isoxazole sulfonamides prepared by the present methods are endothelin antagonists useful, inter alia, for the treatment of hypertension, congestive heart failure and male erectile dysfunction.

13 Claims, No Drawings

OTHER PUBLICATIONS

Wang et al., CA 108:94444w, p. 651 (1988).
Oie, CA 102: 197512x, p. 18 (1995).
Kende et al., Tetrahedron Letters No. 23 (1982), pp. 2369–2372.
Onofrio, et al., CA 92:41908v (1979), p. 782.
T. Saito, CA, vol. 73, No. 23 (1970), 120511w, p. 368.
R. D. Desai et al., Chemical Abstracts, vol. 71, No. 11, (1969) 49825c, p. 382.
R. D. Desai et al., Chemical Abstracts, vol. 71, No. 3, (1969), 12872q, p. 304.
S. Norio et al., Chemical Abstracts, vol. 70, No. 19, (1969), 87639g, p. 324.
CA 65:2241d (1966).
Vree et al., CA 97:84685r, p. 23 (1982).
G. B. Smith, et al., J. Org. Chem., 1994, 59, 8151–8156.
Derwent Abstract No. 62299 E/30, Nippon, Dec. 11, 1980.
Derwent Abstract No. 40927 D23, Nippon, Sep. 11, 1979.
Derwent Abstract No. 35012 K15, Beecham, Sep. 24, 1981.

* cited by examiner

METHODS FOR THE PREPARATION OF BIPHENYL ISOXAZOLE SULFONAMIDES

This application claims benefit of provisional application Ser. No. 60/125,148 filed Mar. 19, 1999.

FIELD OF THE INVENTION

The present invention relates to methods for the preparation of biphenyl isoxazole sulfonamides and intermediates thereof. The present invention also relates to the novel intermediates prepared by these methods. The biphenyl isoxazole sulfonamides prepared by the present methods are endothelin antagonists useful, inter alia, for the treatment of hypertension.

BRIEF DESCRIPTION OF THE INVENTION

The present methods allow preparation of biphenyl sulfonamides of the following formula I:

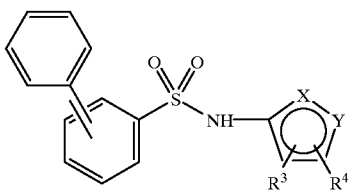

(I)

where the phenyl rings of the biphenyl group may independently be unsubstituted or substituted with one or more substituent groups, enantiomers and diastereomers, and salts, preferably pharmaceutically acceptable salts, thereof. Preferred substituent groups for the biphenyl group include those groups $R^{11}$ to $R^{14}$ described herein and especially, when the biphenyl group is a 2-biphenyl group, the group

in the 4'-position.

Preferred methods of the present invention allow preparation of compounds of the following formula Ia:

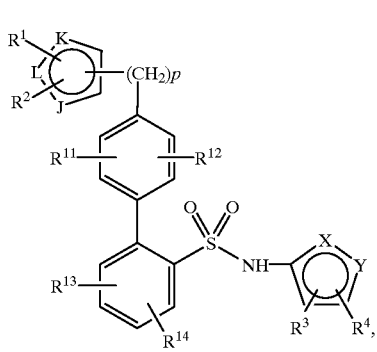

(Ia)

enantiomers and diastereomers, and salts, preferably pharmaceutically acceptable salts, thereof. Throughout this specification, the above symbols are defined as follows:
one of X and Y is N and the other is O;

$R^1$, $R^2$, $R^3$ and $R^4$ are each directly bonded to a ring carbon and are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^5$;
(h) —CO$_2$H or —CO$_2R^5$;
(i) –$Z^4$—NR$^6$R$^7$;
(j) —$Z^4$—N($R^{10}$)—$Z^5$—NR$^8$R$^9$; or
(k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $z^3$;

$R^6$, $R^7$, $R^8$, $R^9$ and $R^{10}$ are each independently
(a) hydrogen; or
(b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
(c) heterocycle, substituted heterocycle or heterocclooxy;
(d) halo;
(e) hydroxyl;
(f) cyano;
(g) nitro;
(h) —C(O)H or —C(O)$R^5$;
(i) —CO$_2$H or —CO$_2R^5$;
(j) —SH, —S(O)$_nR^5$, —S(O)$_m$—OH, —S(O)$_m$—OR$^5$, —O—S(O)m—OR$^5$, —O—S(O)$_m$OH or —O—S(O)$_m$—OR$^5$;
(k) —$Z^4$—NR$^6$R$^7$; or
(l) —$Z^4$—N($R^{10}$)—$Z^5$—NR$^8$R$^9$;

$Z^1$, $Z^2$ and $Z^3$ are each independently
(a) hydrogen;
(b) halo;
(c) hydroxy;
(d) alkyl;
(e) alkenyl;
(f) aryl;
(g) aralkyl;
(h) alkoxy;
(i) aryloxy;

(j) aralkoxy;
(k) heterocycle, substituted heterocycle or heterocyclooxy;
(l) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$—N(Z$^{11}$) —Z$^5$—H;
(t) —Z$^4$—N(Z$^{11}$) —Z$^5$—Z$^6$; or
(u) —Z$^4$—N(Z$^{11}$) —Z$^5$—Nz$^7$Z$^8$;

Z$^4$ and Z$^5$ are each independently
(a) a single bond;
(b) —Z$^9$—s(O)$_n$—Z$^{10}$—;
(c) —Z$^9$—C(O) —Z$^{10}$—;
(d) —Z$^9$—C(s)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

Z$^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

Z$^7$ and Z$^8$ are each independently hydrogen, alkyl, cycloalkyl, cycloalkylalkyl, cycloalkenylalkyl, aryl or aralkyl, or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

Z$^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of Z$^7$, Z$^8$ and Z$^{11}$ together are alkylene or alkenylene, completing a 3- to 8-membered saturated or unsaturated ring together with the atoms to which they are attached;

J is O, S, N or NR$^{15}$;
K and L are N or C, provided that at least one of K or L is C;
R$^{15}$ is hydrogen, alkyl, hydroxyethoxy methyl or methoxyethoxy methyl;
each m is independently 1 or 2;
each n is independently 0, 1 or 2; and
p is 0 or an integer from 1 to 2.

In accordance herewith, a compound of the formula I or salt thereof may be prepared by a method comprising the steps of:

(a) contacting an arylboronic acid of the formula II:

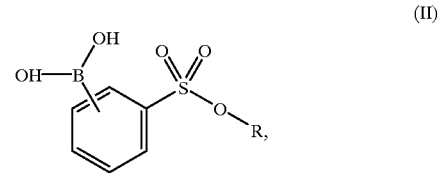

(II)

or pinacol ester or salt thereof, wherein R is an alkyl group and where the phenyl ring of said formula II may be further substituted, such as with one or more groups described for the groups R$^{11}$ to R$^{14}$ herein, with a halophenyl compound of the formula III or salt thereof:

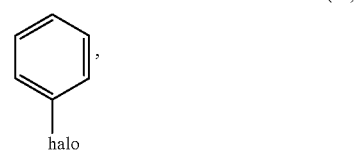

(III)

wherein the halo group is preferably bromo or iodo and wherein the phenyl ring of said formula III may be further substituted, such as with one or more groups described for the groups R$^{11}$ to R$^{14}$ herein, and especially, when the biphenyl group of said compound of the formula I or salt thereof is a 2-biphenyl, the group

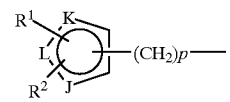

para to the halo group, in the presence of a palladium(0) catalyst and a base containing an alkali metal atom selected from sodium, potassium or lithium, to form a compound of the formula IV or salt thereof:

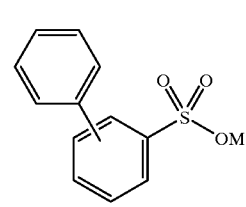

(IV)

and converting said compound IV or salt thereof to a compound V or salt thereof with a chlorinating agent:

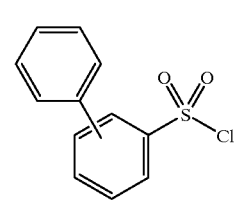

(V)

where the phenyl rings of the biphenyl groups of formulae IV or V may independently be unsubstituted or substituted with one or more substituent groups; and M is sodium, potassium or lithium; and (b) coupling the compound of formula V or salt thereof with a compound of formula VI

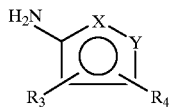
(VI)

in the presence of a base to form said formula I or salt thereof.

In a preferred embodiment, a compound of the formula Ia or salt thereof may be prepared by a method comprising the steps of:

(a) contacting a boronic acid of the formula IIa or salt thereof:

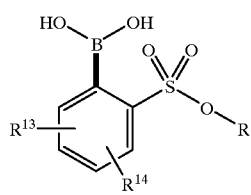
(IIa)

wherein R is an alkyl group, with a halophenyl compound of the formula IIIa or salt thereof:

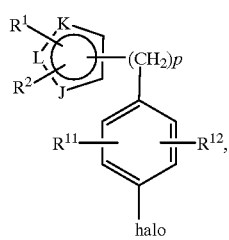
(IIIa)

in the presence of a palladium(0) catalyst and a base containing an alkali metal atom selected from sodium, potassium or lithium, to form a compound of formula IVa or salt thereof:

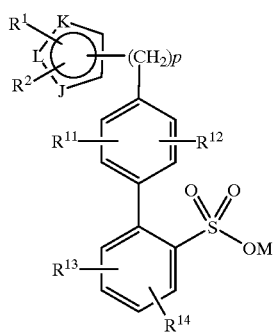
(IVa)

wherein M is lithium, sodium or potassium; and converting compound IVa to compound Va with a chlorinating agent:

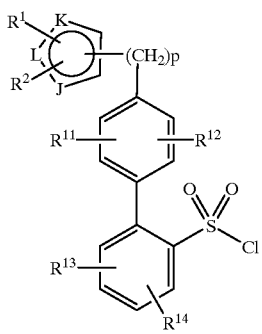
(Va)

and (b) coupling said formula Va compound or salt thereof with a compound of formula VI in the presence of a base to form said compound of the formula Ia or salt thereof.

The present methods for preparing a compound of the formula I or salt thereof are advantageous in that they provide high yields with minimal or no formation of impurities.

Also provided herewith are novel intermediates of the present methods, for example, compounds of the formulae II, IV, V, VIII and XII, and novel methods for preparing such intermediates. The aforementioned step (b), that is, the coupling of the formulae V and VI compounds, is itself a novel step and a further embodiment of the invention.

DETAILED DESCRIPTION OF THE INVENTION

The present invention is described further as follows. Listed below are definitions of terms used in this specification. These definitions apply to the terms as used throughout this specification, individually or as part of another group, unless otherwise indicated in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxyl" refers to alkyl-O—.

The term "chlorinating agent" refers to an agent which supplies chlorine, such as dimethylchloromethyleneammonium chloride (also referred to herein as "Vilsmeier reagent", which may be formed, for example, by the reaction of dimethyl formamide with oxalyl chloride), as well as phosphorus oxychloride, oxalyl chloride, or thionyl chloride.

The term "alcohol" refers to alcohol of 1 to 7 carbon atoms, especially alkyl alcohols such as methyl alcohol, ethyl alcohol, n-propyl alcohol, isopropyl alcohol, butyl alcohol etc.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —(CH2)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH—and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C—and —C≡C—CH(C$_2$H$_5$)CH$_2$—.

The term "alkanoyl" refers to groups of the formula —C(O)alkyl.

The terms "cycloalkyl" and "cycloalkenyll" refer to cyclic hydrocarbon groups of 3 to 8 carbon atoms.

The term "hydroxyalkyl" refers to an alkyl group including one or more hydroxy radicals such as —CH$_2$CH$_2$OH, —CH$_2$CH$_2$OHCH$_2$OH, —CH(CH$_2$OH)$_2$ and the like.

The terms "halogen" and "halo" refer to fluorine, chlorine, bromine and iodine.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The expression "substituted heterocycle" refers to a heterocycle substituted with 1, 2 or 3 of the following:

(a) alkyl, especially lower alkyl;
(b) hydroxy (or protected hydroxy);
(c) halo;
(d) oxo (i.e. =O);
(e) amino, alkylamino or dialkylamino;
(f) alkoxy;
(g) carbocyclo, such as cycloalkyl;
(h) carboxy;
(i) heterocyclooxy;
(j) alkoxycarbonyl, such as unsubstituted lower alkoxycarbonyl;
(k) carbamyl, alkylcarbamyl or dialkylcarbamyl;
(l) mercapto;
(m) nitro;
(n) cyano;
(o) carboalkoxy;
(p) sulfonamido, sulfonamidoalkyl or sulfonamidodialkyl;

(q) 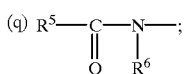

(r) 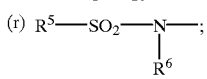

(s) aryl;
(t) alkylcarbonyloxy;
(u) arylcarbonyloxy;
(v) arylthio;
(w) aryloxy;
(x) alkylthio;
(y) formyl;
(z) arylalkyl; or
(a') aryl substituted with alkyl, cycloalkyl, alkoxy, hydroxy, amino, alkylamino, dialkylamino, halo or trihaloalkyl.

The term "heterocyclooxy" denotes a heterocyclic group bonded through an oxygen bridge.

The term "pinacol ester thereof" denotes a compound wherein the group

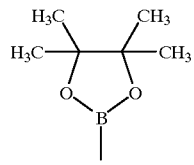

appears in place of the boronic acid group —B(OH)$_2$.

Throughout the specification, groups and substituents thereof may be chosen to provide stable moieties and compounds.

The compounds of formula I and intermediates thereof may form salts which are also within the scope of this invention. Pharmaceutically acceptable (i.e., non-toxic, physiologically acceptable) salts are preferred, although other salts are also useful, for example, in isolating or purifying the compounds of this invention.

The compounds of formula I and intermediates thereof may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting these compounds with the desired ion in a medium in which the salt precipitates or in an aqueous medium followed by lyophilization.

When groups such as the $R^1$ to $R^4$ or $R^{11}$ to $R^{14}$ substituents comprise a basic moiety, such as amino or substituted amino, the compounds of formula I and intermediates thereof may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting these compounds in an equivalent amount of the acid in a medium in which the salt precipitates or in an aqueous medium followed by lyophilization.

In addition, when groups such as the $R^1$ to $R^4$ or $R^{11}$ to $R^{14}$ substituents comprise a basic moiety such as amino, zwitterions ("inner salts") may be formed.

Certain groups such as the $R^1$ to $R^4$ and $R^{11}$ to $R^{14}$ substituents of the compounds of the invention may contain asymmetric carbon atoms. The compounds of the invention such as those of the formula I and salts thereof may exist, therefore, in enantiomeric and diastereomeric forms and in racemic mixtures thereof. All are within the scope of this invention. Additionally, compounds such as those of formula I and salts thereof may exist as enantiomers even in the absence of asymmetric carbons. All such enantiomers are within the scope of this invention.

U.S. Pat. Nos. 5,612,359, 5,846,990 and 5,856,507 describing endothelin antagonists including those of the formula I which may be prepared herein, starting materials and methods, are each incorporated herein by reference in their entirety. See especially U.S. Pat. No. 5,856,507 with respect to the formation of pinacol esters.

Coupling of Formulae II and III Compounds

A compound of the formula I or salt thereof may be prepared by coupling an alkyl boronic acid of the formula II or pinacol ester or salt thereof with a halophenyl compound of the formula III or salt thereof (preferably, where halo is iodo), and then converting the resulting compound of formula IV to the compound of formula V and reacting the compound of formula V with a compound of formula VI.

Coupling of compounds of the formulae II (or pinacol esters) and III or salts thereof is conducted in the presence of a palladium(0) catalyst, preferably palladium acetate/triphenylphosphine or other palladium (II) salt/triphenylphosphine, tetrakisphenylphosphine palladium or tris(dibenzylideneacetone)dipalladium(0) (also referred to herein as ("Pd$_2$(dba)3"), and a base containing an alkali metal atom selected from sodium, potassium or lithium, preferably aqueous potassium carbonate or sodium carbonate, to form a compound of the formula IV or salt thereof. See the conditions for catalysis described by A. Suzuki et al., Pure & Applied Chemistry, 63, 419–422 (1991); A. Martin et al., Acta. Chem. Scand., 47, 221 (1993); H. Jendralla et al., Liebig Ann., 1253 (1995), all incorporated herein by reference.

When the halophenyl compound III is a compound IIIa, protection of the heteroatoms J and K or L may be desirable, in certain instances, to facilitate the coupling reaction. For example, when J and K or L are N, one of the groups may be protected by a suitable protecting group such as t-butoxycarbonyl, etc. Specific $R^{11}$–$R^{14}$ groups may be chosen to be compatible with the reaction conditions. Additionally, specific $R^{11}$–$R^{14}$ groups may be converted into alternative $R^{11}$–$R^{14}$ groups, either before or after coupling, using any suitable methods such as those known in the art.

The coupling method is preferably conducted at a temperature of from about 25° C. to about 100° C. (most preferably from about 45° C. to about 65° C.), at a pressure of about 1 atm, and under an atmosphere of argon or nitrogen. Molar ratios of the boronic acid II (or pinacol ester) or salt thereof to the halophenyl compound III or salt thereof are preferably from about 1:1 to about 1.4:1. Amounts of palladium(0) catalyst and base are selected to catalyze the coupling reaction and are preferably from about 2.5 mol % to about 10 mol %, and from about 2.5 equivalents to about 7 equivalents, respectively. Solvents are preferably employed which are selected from aqueous or organic liquids such as acetone, ethanol, toluene, tetrahydrofuran, dimethoxyethane and water, or mixtures thereof, preferably a mixture of tetrahydrofuran and dimethoxyethane.

Residual palladium catalyst is preferably removed, from the compound of formula IV or salt thereof, by contact with a chelating agent such as trithiocyanuric acid ("TMT").

Compounds of the formula III and salts thereof are commercially available or may be prepared by any suitable method, such as methods analogous to those described in U.S. Pat. No. 5,846,990. Preferably, oxazole compounds of the formula IIIa or salts thereof are prepared by the novel methods for their preparation described herein.

Compounds of the formula II and salts thereof may be prepared by any suitable method, and are preferably prepared by the novel methods for their preparation described herein.

Preparation of Formula II Compounds

The boronic acids of the formula II and salts thereof may themselves be formed by novel methods provided herein. In accordance herewith, a boronic acid of the formula II or salt thereof may be prepared by a method comprising the steps of:

(a) contacting a compound of the formula VII or salt thereof:

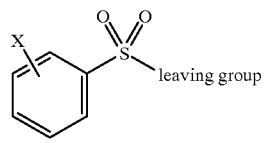

(VII)

wherein X is H, Br, Cl or I, and where the phenyl group of said formula VII may be further substituted, such as with one or more groups described for the groups $R^{11}$ to $R^{14}$ herein, with an alcohol in the presence of an organic base, to form a compound of the formula VIII or salt thereof:

(VIII)

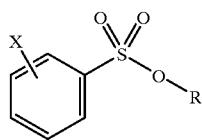

where the phenyl group of said formula VIII may be further substituted, such as with one or more groups described for the groups $R^{11}$ to $R^{14}$ herein; and (b) lithiating the compound VIII with an alkyl or aryl lithium compound and contacting the lithiated product formed with a trialkyborate, followed by hydrolysis, to form the boronic acid of formula II.

In a preferred embodiment, a boronic acid of the formula IIa or salt thereof may be prepared by a method comprising the steps of:

(a) contacting a compound of the formula VIIa or salt thereof:

(VIIa)

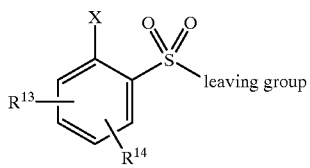

wherein X is H, Br, Cl or I, with an alcohol in the presence of an organic base to form a compound of the formula VIIIa:

(VIIIa)

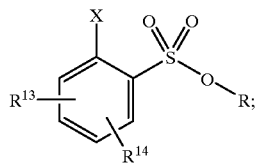

and (b) lithiating said compound of the formula VIIIa or salt thereof with an alkyl or aryl lithium compound and contacting the lithiated product formed with a trialkylborate, followed by hydrolysis, to form a boronic acid of the formula IIa or salt thereof.

The term "leaving group", as used herein, denotes any suitable leaving group such as a halo group, preferably chloro. Any suitable organic base may be employed in step (a). Preferred organic bases include amines, particularly tertiary amines, such as N-methylmorpholine (especially preferred when X is hydrogen), pyridine or a trialkylamine, and aryl or alkyllithium compounds such as n-butyllithium or phenyllithium.

As described above, compounds of the formula VIIIa and salts thereof may be prepared by contacting a compound of the formula VIIa or salt thereof with an alcohol. Preferred alcohols include alkyl alcohols, such as methanol, ethanol or i-propyl alcohol. The formula VIIIa compound or salt thereof obtained is then lithiated with an alkyl or aryl lithium compound, preferably with n-butyl lithium or phenyl lithium, at temperatures which are preferably from about −40° C. to about −105° C., especially, from about −70° C. to about −100° C., to form the compound:

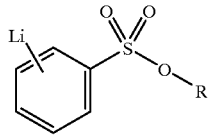

where the phenyl group of said compound may be further substituted, such as with one or more groups described for the groups $R^{11}$ to $R^{14}$ herein, or salt thereof, preferably the compound:

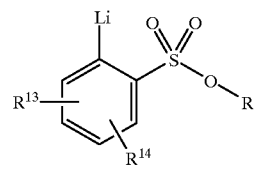

or salt thereof. Lithiation occurs selectively at the position ortho to the sulfonyl group on the phenyl ring. Treatment of the lithiated compound or salt thereof with a trialkylborate, preferably triisopropylborate or, trimethylborate, at temperatures which are preferably from about −40° C. to about −105° C. especially, from about −70° C. to about −100° C., provides the following boronate:

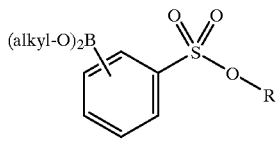

where the phenyl group of said compound may be further substituted, such as with one or more groups described for the groups $R^{11}$ to $R^{14}$ herein, or salt thereof, preferably the boronate:

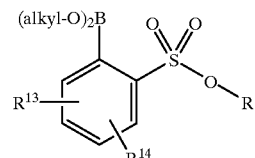

or salt thereof, which may then be hydrolyzed with a suitable acid, preferably an aqueous mineral acid such as aqueous sulfuric acid to form the boronic acid IIa or salt thereof. The hydrolysis step, forming the boronic acid IIa or salt thereof, is advantageous as the boronic acid possesses enhanced stability relative to the boronate ester from which it is obtained. For methods and descriptions of the starting material of the formulae VIIa and salts thereof see European Patent Application Publication No. 569,193 (1993). Certain of these compounds are also commercially available.

Preparation of Formula III Compounds

Halophenyl compounds of the formula III and salts thereof may be prepared by methods analogous to those described in U.S. Pat. No. 5,846,990. Preferred compounds of the formula IIIa and salts thereof bearing an oxazole ring may also be formed by novel methods provided herein. In accordance herewith, a formula IIIa(1) oxazole or salt thereof may be prepared by a method comprising the steps of:

(a) contacting a phenyl acid halide IX or salt thereof:

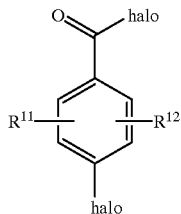

(IX)

with an amine acetal X or salt thereof:

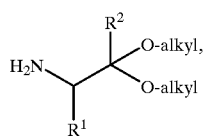

(X)

in the presence of a base and a solvent, to form an amide acetal of the formula XI or salt thereof:

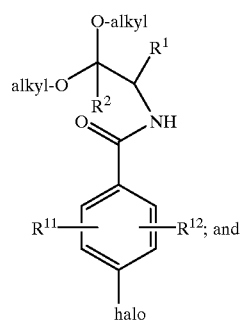

(XI)

(b) cyclizing the amide acetal of the formula XI or salt thereof, in the presence of a Lewis acid and a tertiary amine, to form an oxazoline phenyl halide of the formula XII or salt thereof:

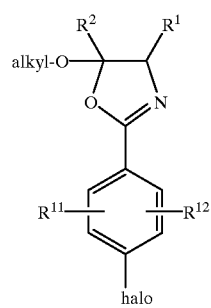

(XII)

and (c) reacting the oxazoline phenyl halide of the formula XII or salt thereof with a base to form an oxazole phenyl halide of the formula IIIa(1) or salt thereof:

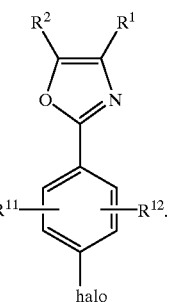

(IIIa(1))

The starting phenyl acid halide IX or salt thereof is commercially available or may readily be prepared by one of ordinary skill in the art. The halo group of the acid halide moiety is preferably chloro; the halo group in the position para to the acid halide moiety is preferably bromo, chloro, or iodo, most preferably iodo. The starting amine acetal X or salt thereof is also commercially available or may readily be prepared by one of ordinary skill in the art. The alkyl groups of the acetal moiety are preferably methyl or ethyl, most preferably, methyl.

The base employed in step (a) may be any suitable base, and is preferably an alkali metal carbonate, bicarbonate or hydroxide, most preferably, potassium bicarbonate in a solvent such as water and/or acetone or potassium carbonate in a solvent such as methylene chloride.

Cyclization is conducted by contacting the amide acetal XI or salt thereof with a Lewis acid, for example, borontrifluoride-etherate, borontribromide or trimethylsilylchlorosulfonate, most preferably borontrifluoride-etherate, and a tertiary amine, for example, diisopropylethylamine, 4-methylmorpholine, 2,6-lutidine, most preferably diisopropylethylamine, in an organic solvent such as toluene, dichloromethane or tetrahydrofuran. Cyclization conducted according to the present method using a Lewis acid and tertiary amine is advantageous in not requiring the use of high temperatures, and in not generating undesirable by-products, for example, as may occur when employing Eaton's reagent (i.e., methanesulfonic acid and phosphorous pentoxide), or polyphosphoric acid. The cyclization is preferably conducted at a temperature of from about 0° C. to about 50° C., at a pressure of about 1 atm, and under an atmosphere of argon or nitrogen. The base employed in step (c) may be any suitable base, and is preferably an alkoxide base, most preferably, potassium or sodium tert-butoxide.

Conversion of Compounds IV to V and Coupling with Compounds VI to Form Formula I Compounds Compounds of formula I such as those of formula Ia and salts thereof may be formed by the novel methods provided herein.

Compounds of the formula IV may be converted to compounds of the formula V by contact with any suitable chlorinating agent, such as dimethylchloromethyleneammonium chloride, phosphorus oxychloride, oxalyl chloride or thionyl chloride, preferably in a solvent such as toluene.

Compounds of the formula I may be prepared by contacting the formula V compounds with compounds of the formula VI in the presence of a base, preferably sodium hydride or an alkoxide base, most preferably, sodium or potassium tertiary butoxide. When employing sodium t-butoxide, the reaction is preferably run at room temperature or lower temperatures; use of lower temperatures (e.g., −78° C.) is preferred when potassium t-butoxide is employed. The compound of the formula VI may be pre-mixed with the base to form an anion prior to contact with the formula V compound.

Crystallization provides a suitable crystalline form of the compound of the formula I (especially, Ia) or salt thereof, subsequent to the coupling of the compound of the formula V or salt thereof with the compound VI. Most preferably, crystallization is conducted by the methods of the Examples herein.

Preferred Compounds

It is preferred that the compounds employed in or prepared by the present methods contain one or more, preferably all where appropriate, of the following substituents:

X is O and N is Y;

the ring bearing K, L and J is 2-oxazole;

p is zero;

$R^1$ and $R^2$ are each independently hydrogen, alkyl, alkoxy, aryl, hydroxyalkyl, —$CO_2R^5$ or —$Z^4$—$NR^6R^7$, most preferably lower alkyl or hydrogen;

$R^3$ and $R^4$ are each independently alkyl, most preferably lower alkyl, especially methyl; and $R^{11}$, $R^{12}$, $R^{13}$ and $R^{14}$ are each independently hydrogen, hydroxy, amino, heterocyclo, alkenyl, alkoxy, carboxamide or substituted lower alkyl, most preferably, $R^{12}$ to $R^{14}$ are hydrogen and $R^{11}$ is hydrogen, hydroxy, amino, heterocyclo, alkenyl, alkoxy, carboxamide or substituted lower alkyl (such as —$CH_2$—N($CH_3$)—C(O)—$CH_2$—C($CH_3$)$_3$).

Compounds of the formula I of particular interest include N-(3,4-dimethyl-5-isoxazolyl)-4'-(2-oxazolyl)-[1,1'-biphenyl]-2-sulfonamide and salts thereof, and N-[[2'-[[(4, 5-dimethyl-3-isoxazolyl)amino]sulfonyl]-4-(2-oxazolyl)[1, 1'-biphenyl]-2-yl]methyl]-N,3,3-trimethylbutanamide and salts thereof.

Utility of Compounds of Formula I and Salts Thereof as Endothelin Antagonists

The compounds of the formula I and salts thereof are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis). The compounds of the formula I are preferably useful in congestive heart failure and male erectile dysfunction.

The compounds of the formula I and salts thereof can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds;

neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; anti-arrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The present invention will now be further described by the following working examples, which illustrate preferred embodiments of the invention.

EXAMPLE 1

N-(2,2-Dimethoxyethyl)-4-iodobenzamide (amide acetal)

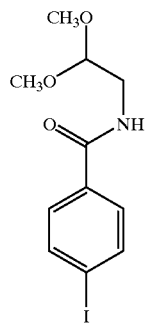

A solution of 4-iodobenzoyl chloride (100 g, 375.6 mmol) in 300 mL of acetone was added to a solution of aminoacetaldehyde dimethylacetal (41.4 g, 1.05 equiv.) and potassium hydrogen carbonate (39.5 g, 1.05 equiv.) in 270 mL of acetone and 450 mL of water. After completion of the reaction, acetone was removed under reduced pressure at no more than 35° C. to induce crystallization. The crystal slurry was filtered, washed and dried in vacuo at <50° C., to give 120 g (95 M %, HPLC area % 96) of the title compound.

EXAMPLE 2

2-(4-Iodophenyl) oxazole (Iodooxazole)

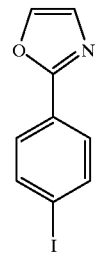

Under an inert atmosphere, methanesulfonic acid (141 g, 1.46 mol) was added to a mixture of amide acetal (25 g, 74.6 mmol) and phosphorus pentoxide (25 g, 176 mmol). The reaction mixture was heated at 140° C. for about 12 hours. The reaction mixture was cooled to 0° C. and 150 mL of water was added while maintaining the reaction temperature below 40° C. The pH of the reaction mixture was adjusted to 12.5–13 with 50% sodium hydroxide and the reaction mixture was heated at ca. 45° C. to hydrolyze the carcinogenic byproduct methyl methanesulfonate. The reaction mixture was cooled to ambient temperature and 100 mL of tetrahydrofuran was added. The pH was adjusted to 5 with concentrated hydrochloric acid and the layers were separated. The spent aqueous phase was extracted twice with 100 mL of acetone. The rich organic extracts were combined and 200 mL of water was added to effect crystallization. The crystal slurry was filtered, washed and dried in vacuo at <50° C., to give 17 g (84 M %, HPLC area % >99) of the title compound.

Polyphosphoric acid may alternatively be employed as the cyclization agent.

Alternative Preparation for the Title Compound

Under an inert atmosphere, borontrifluoride etherate (88 mL, 0.72 mol) was added dropwise to a solution of amide acetal (30 g, 0.089 mol) and diisopropylethylamine (124.8 mL, 0.72 mol) in 200 mL of dichloromethane below 10° C. The reaction mixture was heated to ca. 40° C. for 3–6 hours. The reaction mixture was cooled to less than −10° C. and a solution of potassium tert-butoxide (110.5 g, 0.98 mol) in tetrahydrofuran (550 mL) was added. The reaction mixture was again heated to ca. 40° C. for 3–6 hours. The reaction mixture was cooled to room temperature and 300 mL of water were added. The pH of the biphasic mixture was adjusted to ca. 7 with concentrated hydrochloric acid. The layers were separated. The rich organic layer was concentrated to dryness. The crude product was dissolved in 300 mL acetone and filtered to remove insolubles. About 200 mL of water were added to the rich acetone solution to effect crystallization. The crystal slurry was filtered, washed and dried in vacuo at <50° C., to give 17 g (70 M %, HPLC area >99) of the title compound.

EXAMPLE 3

2-Bromobenzenesulfonic acid, 1-methylethyl ester

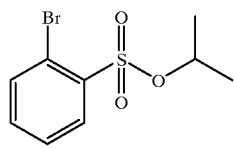

2-Bromobenzenesulfonyl chloride (50 g, 0.19 mol) was suspended in 2-propanol (45 mL, 3 equiv.) and the slurry was cooled to less than 10° C. Pyridine (32 mL, 2 equiv.) was added in portions while maintaining the reaction temperature below 10° C. After reaction completion (ca. 3 hours), 11 mL of glacial acetic acid followed by 250 mL of methyl tert-butyl ether (MTBE) were added. The layers were separated and the rich organic layer was successively washed with 125 mL of iN aqueous hydrochloric acid and 150 mL of saturated sodium bicarbonate solutions. The rich MTBE solution was solvent exchanged into hexane (i.e., the addition of hexane with concurrent distillation of MTBE) to induce crystallization. The crystal slurry was filtered, washed and dried in vacuo at no more than 25° C., to give 48 g (87 M %, HPLC area % >99) of the title compound.

EXAMPLE 4

Benzenesulfonic acid, 1-methylethyl ester

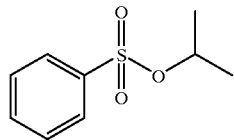

Benzenesulfonyl chloride (50 g, 283 mmol) was added to a solution of 4-methylmorpholine (57 g, 2 equiv.) and isopropyl alcohol (66 g, 3.9 equiv.). After reaction completion (ca. 3 hours), 250 mL of methyl tert-butyl ether (MTBE) and 60 mL of 3M sulfuric acid were added. The rich MTBE layer was washed with aqueous sodium chloride solution. The rich MTBE solution was solvent exchanged into tetrahydrofuran solution. The rich tetrahydrofuran solution containing 56 g (96 M %, HPLC area % 97) of the title compound was used as is in the next step (Example 5).

EXAMPLE 5

2-Boronbenzenesulfonic acid, 1-methylethyl ester

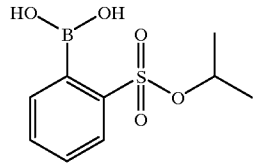

To the solution of the product from Example 3 (56 g, 200 mmol) in 280 mL of THF was added triisopropylborate (84 mL, 1.82 equiv.) and the reaction mixture was cooled to less than −65° C. To the cooled solution, n-butyllithium (144 mL, 0.9 equiv., 1.07 M in hexanes) was slowly added while maintaining the temperature below −65° C. The reaction mixture was stirred for at least 0.5 hours and then was quenched with IM sulfuric acid (200 mL). The reaction mixture was allowed to warm to ca. 20° C. The layers were separated and the rich organic layer containing 35 g (92 M %, HPLC area t 98) of the title compound was used as is in the next step (Example 6).

Alternative Preparation for the Title Compound

The THF solution from Example 4 containing 40 g (200 mmol) of product was cooled to less than −65° C. To the cooled solution, n-butyllithium (144 mL, 0.9 equiv., 1.07 M in hexanes) was slowly added while maintaining the temperature below −65° C. The reaction mixture was stirred for at least 0.5 hours and triisopropylborate (84 mL, 1.82 equiv.) was added while maintaining the temperature below −65° C. The reaction mixture was quenched with 1M sulfuric acid (200 mL) and the reaction mixture was allowed to warm to ca. 20° C. The layers were separated and the rich organic layer containing 33 g (87 M %, HPLC area % 94) of the title compound was used as is in the next step (Example 6).

EXAMPLE 6

4'-(2-Oxazolyl)[1,1'-biphenyl]-2-sulfonic acid, sodium salt

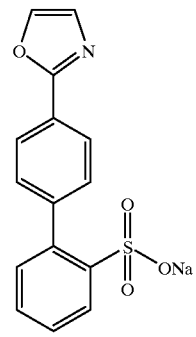

The THF-Hexane-MTBE solution containing 23 g (93.3 mmol) of the title compound from Example 5 was concentrated to a concentration of ca. 7 mL/g. A portion of this solution containing ca. 4.7 g (19 mmol, 0.26 equiv.) was added to a solution of 20 g (75 mmol) of the title compound from Example 2 dissolved in 100 mL of degassed tetrahydrofuran. To this solution, tris(dibenzylidene acetone) dipalladium (0) (0.5 g, 0.6 M %) and degassed aqueous sodium carbonate solution (300 mL, 3 equiv.) were added. The reaction mixture was heated to ca. 50° C. to initiate the coupling reaction. During the reaction, Pd$_2$(dba)$_3$ (0.5 g per addition) and rich organic concentrate containing the title compound from Example 5 (4.7 g, 0.26 equiv. per addition) were added in several portions until all the iodooxazole was consumed. The reaction mixture was further heated at ca. 55° C. for an additional 4 hours. The reaction mixture was filtered and washed with methyl-tert-butyl ether. The pH of the product-rich aqueous solution was adjusted to ca. 4, treated with trithiocyanuric acid (1 g) and filtered to remove Pd containing by-products. The pH of the product-rich aqueous solution was adjusted to ca. 7 and was saturated with solid NaCl (118 g) to initiate the crystallization of the product. The salted-out product was dried in vacuo at less than 70° C. For recrystallization, the dried product was dissolved in 350 mL of 190 proof ethanol at ca. 75° C. The solution was filtered and concentrated to ca. 100 mL and cooled to ca. 30° C. to initiate crystallization. About 200 mL of methyl-tert-butyl ether was added to maximize the yield. The crystal slurry was filtered, washed and dried in vacuo less than 70° C., to give 19 g (74 M %, HPLC area % 100) of the title compound.

EXAMPLE 7

N-(3,4-Dimethyl-5-isoxazolyl)-4'-(2-oxazolyl)-[1,1'-biphenyl]-2-sulfonamide

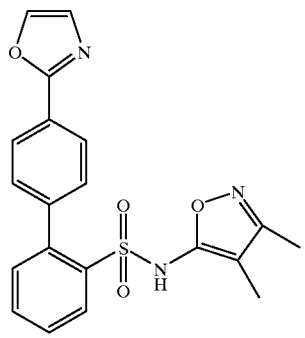

About 15.5 g (47.9 mmol) of the title compound from Example 6 was suspended in 200 mL of toluene and Vilsmeier reagent (9 g, 71.8 mmol) was added at room temperature. The mixture was stirred until the chlorination reaction was complete (ca. 3 hours). The reaction mixture was quenched with 50 mL of water and the pH was adjusted to 7–10 with 10N NaOH. Layers were separated and water was removed azeotropically from the rich toluene solution to a moisture content of less than 0.05%. This rich toluene solution was added to a solution of 5-amino-3,4-dimethylisoxazole (6.1 g, 54.4 mmol) in 90 mL of tetrahydrofuran. The reaction mixture was cooled to –15° C. and a slurry of sodium t-butoxide (10 g, 104.3 mmol) in 70 mL of tetrahydrofuran was added. After the coupling reaction was complete, the mixture was quenched with 100 mL of water and then warmed to ca. 50° C., to afford two clear phases. The spent organic layer was extracted with water (50 mL). To the combined rich aqueous solution, 85 mL of 190 proof ethanol and 15 mL of tetrahydrofuran were added. The pH was adjusted to ca. 2 with conc. HCl to precipitate the product. The resultant slurry was heated to ca. 75° C. to dissolve the product. The product was crystallized by slow cooling to room temperature. Additional water (120 mL) was added to maximize the yield. The crystal slurry was filtered, washed and dried in vacuo at less than 60° C., to give 16 g (85 M %, HPLC area % 99.6) of the title compound.

What is claimed is:

1. A method for the preparation of a biphenyl sulfonamide of the following formula I:

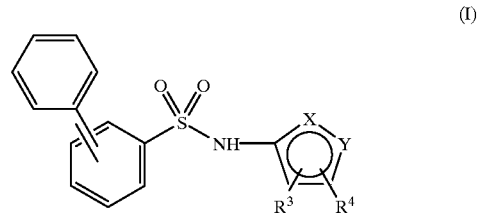

(I)

where the phenyl rings of the biphenyl group may independently be unsubstituted or substituted with one or more substituent groups, enantiomers and diastereomers, and salts thereof, wherein:

one of X and Y is N and the other is O;

$R^3$ and $R^4$ are each directly bonded to a ring carbon and are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;

(c) halo;

(d) hydroxyl;

(e) cyano;

(f) nitro;

(g) —C(O)H or —C(O)R$^5$;

(h) —CO$_2$H or —CO$_2$R$^5$;

(i) —Z$^4$—NR$^6$R$^7$;

(j) —Z$^4$—N(R$^{10}$)—Z$^5$—NR$^8$R$^9$; or (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently (a) hydrogen; or (b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$Z^1$, $Z^2$ and $Z^3$ are each independently
(a) hydrogen;
(b) halo;
(c) hydroxy;
(d) alkyl;
(e) alkenyl;
(f) aryl;
(g) aralkyl;
(h) alkoxy;
(i) aryloxy;
(j) aralkoxy;
(k) heterocycle, substituted heterocycle or heterocyclooxy;
(l) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$—N(Z$^{11}$)—Z$^5$—H;
(t) —Z$^4$—N(Z$^{11}$)—Z$^5$—Z$^6$; or
(u) —Z$^4$—N(Z$^{11}$)—Z$^5$—NZ$^7$Z$^8$;

$Z^4$ and $Z^5$ are each independently
(a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

$Z^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocycle or substituted heterocycle;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

each m is independently 1 or 2; and each n is independently 0, 1 or 2; comprising the steps of:
(a) contacting a boronic acid of the formula II:

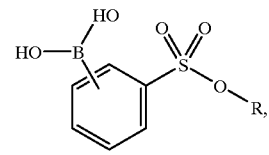

(II)

or pinacol ester or salt thereof, wherein R is an alkyl group and where the phenyl ring of said formula II may be further substituted, with a halophenyl compound of the formula III or salt thereof:

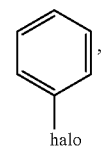

(III)

wherein the phenyl ring of said formula III may be further substituted, in the presence of a palladium(0) catalyst and a base containing an alkali metal atom selected from sodium, potassium or lithium, to form a compound of the formula IV or salt thereof:

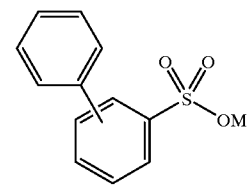

(IV)

and converting said compound IV or salt thereof to a compound V or salt thereof with a chlorinating agent:

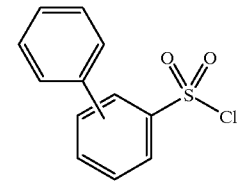

(V)

where the phenyl rings of the biphenyl groups of formulae IV or V may independently be unsubstituted or substituted with one or more substituent groups; and M is sodium, potassium or lithium; and (b) coupling said compound of the formula V or salt thereof with a compound of formula VI:

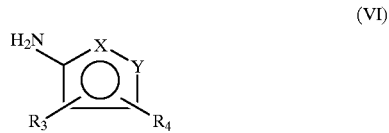

in the presence of base to form said compound of the formula I or salt thereof.

2. The method of claim 1, wherein said compound of the formula I is a compound of the following formula Ia or salt thereof:

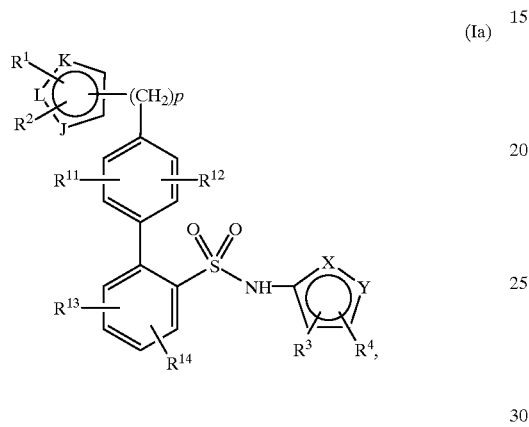

wherein:

R$^1$ and R$^2$ are each directly bonded to a ring carbon and are each independently selected from those groups (a) through (j) recited above for R$^3$ and R$^4$;

R$^{11}$, R$^{12}$, R$^{13}$ and R$^{14}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with Z$^1$, Z$^2$ and Z$^3$,
  (c) heterocycle, substituted heterocycle or heterocyclooxy;
  (d) halo;
  (e) hydroxyl;
  (f) cyano;
  (g) nitro;
  (h) —C(O)H or —C(O)R$^5$;
  (i) —CO$_2$H or —CO$_2$R$^5$;
  (j) —SH, —S(O)$_n$R$^5$, —S(O)$_m$—OH, —S(O)$_m$—OR$^5$, —O—S(O)m—OR$^5$, —O—S(O)$_m$OH or —O—S(O)$_m$—OR$^5$;
  (k) —Z$^4$—NR$^6$R$^7$; or
  (l) —Z$^4$—N(R$^{10}$)—Z$^5$—NR$^8$R$^9$;

J is O, S, N or NR$^{15}$;

K and L are N or C, provided that at least one of K or L is C;

R$^{15}$ is hydrogen, alkyl, hydroxyethoxy methyl or methoxyethoxy methyl; and p is 0 or an integer from 1 to 2; comprising the steps of:
  (a) contacting a boronic acid of the formula IIa or salt thereof:

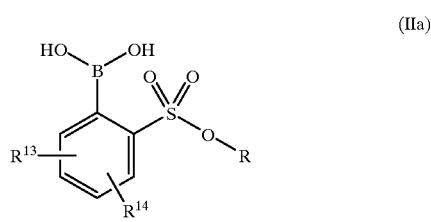

wherein R is an alkyl group, with a halophenyl compound of the formula IIIa or salt thereof:

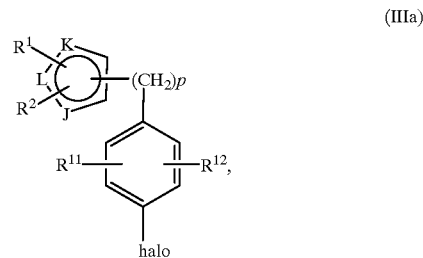

in the presence of a palladium(0) catalyst and a base containing an alkali metal atom selected from sodium, potassium or lithium, to form a compound of the formula IVa or salt thereof:

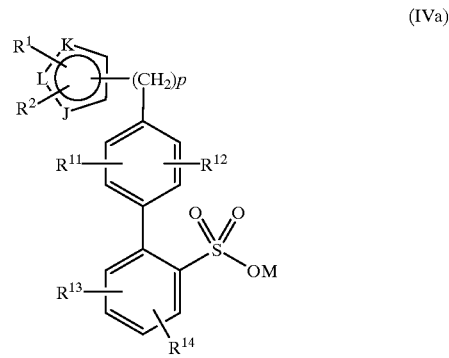

wherein M is lithium, sodium or potassium; and converting compound IVa to compound Va with a chlorinating agent:

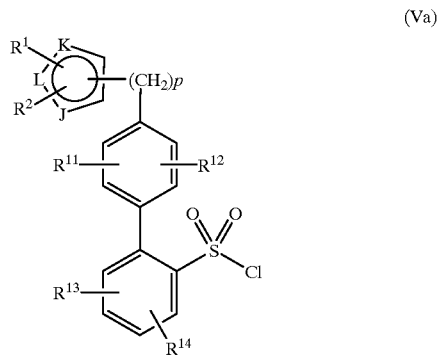

and (b) coupling said formula Va compound or salt thereof with a compound of formula VI in the presence of a base to form said compound of the formula Ia or salt thereof.

3. The method of claim 2, wherein said palladium(0) catalyst is a palladium (II) salt and triphenylphosphine.

4. The method of claim 3, wherein said palladium (II) salt is palladium acetate.

5. The method of claim 2, wherein said palladium caralyst is tris(dibenzylideneacetone)dipallidium (O).

6. The method of claim 2, wherein said base in step (a) is aqueous potassium carbonate or sodium carbonate.

7. The method of claim 2, wherein the halo group in said compound of the formula IIIa or salt thereof is bromo or iodo.

8. The method of claim 2, wherein said compound of the formula Ia or salt thereof is crystallized from solution subsequent to step (b).

9. The method of claim 2, wherein residual palladium is removed subsequent to contacting said compounds IIa and IIIa by use of a chelating agent.

10. The method of claim 2, wherein the chlorinating agent is Vilsmeier reagent, thionyl chloride, oxalyl chloride or phosphorous oxychloride.

11. The method of claim 2, wherein the base in step (b) is sodium hydride, potassium tert-butoxide or sodium tert-butoxide.

12. The method of claim 2, wherein said compound of the formula Ia is N-(3,4-dimethyl-5-isoxazolyl)-4'-(2-oxazolyl)-[1,1'-biphenyl]-2-sulfonamide or salt thereof.

13. The method of claim 2, wherein said compound of the formula Ia is N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide or salt thereof.

* * * * *